United States Patent

Falb et al.

Patent Number: 5,335,652
Date of Patent: Aug. 9, 1994

[54] GAS RATIO CONTROL DEVICE FOR ANESTHETIC APPARATUS

[75] Inventors: Wolfgang Falb, Krummesse; Karl-Ludwig Gippert; Ulrich Heim, both of Lübeck; Uvo Hölscher, Stockelsdorf; Siegfried Kiske, Krummesse; Götz Kullik, Lübeck; Ralf-Ernst Löser, Kreuzkamp; Christoph Maurer, Schwartau, all of Fed. Rep. of Germany

[73] Assignee: Dragerwerk Aktiengesellschaft, Lubeck, Fed. Rep. of Germany

[21] Appl. No.: 833,308

[22] Filed: Feb. 10, 1992

[30] Foreign Application Priority Data

Apr. 6, 1991 [DE] Fed. Rep. of Germany ....... 4111139

[51] Int. Cl.$^5$ ............................................. A61M 17/00
[52] U.S. Cl. ........................ 128/203.14; 128/203.25; 128/204.25; 128/205.24
[58] Field of Search ............... 73/861.47; 128/203.12, 128/203.25, 203.14, 204.18, 204.21, 204.22, 204.25, 205.24, 205.11

[56] References Cited

U.S. PATENT DOCUMENTS

| | | | |
|---|---|---|---|
| 1,585,170 | 5/1926 | Roucka | 73/861.47 X |
| 2,132,338 | 10/1938 | Ziebolz | 73/861.47 X |
| 3,047,210 | 7/1962 | Best | 73/861.47 X |
| 4,191,952 | 3/1980 | Schreiber | 340/611 |
| 4,328,823 | 5/1982 | Schreiber | 137/88 |
| 4,442,856 | 4/1984 | Betz | 137/98 |
| 4,555,952 | 12/1985 | Jenkins | 73/861.47 |
| 4,972,831 | 11/1990 | von dem Hagen | 128/204.21 |
| 5,049,317 | 9/1991 | Kiske | 261/16 |

FOREIGN PATENT DOCUMENTS

| | | | |
|---|---|---|---|
| 98193 | 1/1984 | European Pat. Off. | 128/203.12 |
| 117699 | 9/1984 | European Pat. Off. | 128/203.12 |
| 966941 | 3/1950 | France | 128/203.25 |
| 2548908 | 1/1985 | France | 128/203.12 |
| 2136703 | 9/1984 | United Kingdom | 128/203.12 |
| 2148721 | 6/1985 | United Kingdom | 128/203.12 |

Primary Examiner—Edgar S. Burr
Assistant Examiner—Eric P. Raciti
Attorney, Agent, or Firm—McGlew and Tuttle

[57] ABSTRACT

A gas ratio control device for anesthetic apparatus with an anesthetic gas feed line 1, which has a control valve 12 and a first measuring resistance 6, and an oxygen feed line 2 with a second measuring resistance 10, wherein the differential pressure determined from the measuring resistances is sent to a proportional member 13 for regulating oxygen feed to anesthetic gas feed. So oxygen concentration will not drop below a minimum oxygen concentration value in the case of anesthetics to be metered at both low and high doses, one of the measuring resistances 6, 10 can be replaced or bridged over with a bypass line 14, which contains a throttle point 15 (FIG. 1).

10 Claims, 3 Drawing Sheets

GAS RATIO CONTROL DEVICE FOR ANESTHETIC APPARATUS

FIELD OF THE INVENTION

The present invention pertains to a gas ratio control device for anesthetic apparatus with an anesthetic gas feed line which has, in series connection, a control valve, an anesthetic gas adjusting valve, and a first measuring resistance, and with an oxygen feed line with an oxygen adjusting valve and a second measuring resistance, wherein the differential pressure determined from the measuring resistances is sent to a proportional member that controls the control valve.

BACKGROUND OF THE INVENTION

A gas ratio control device of the above-described class is shown in U.S. Pat. No. 4,972,831 (corresponding to DE-A1-38,10,745).

In the prior-art gas ratio control device, an anesthetic gas is carried in an anesthetic gas feed line which contains a pressure reducer and a control valve, which precede an anesthetic gas adjusting valve. The metered anesthetic gas flows via a first measuring resistance and a flow-measuring tube for indicating the metering to a fresh gas outlet. The oxygen is carried via an oxygen feed line to this fresh gas outlet, which contains a pressure reducer and an oxygen adjusting valve, as well as a second measuring resistance and a flow-measuring tube. The gas streams generate dynamic pressures at the measuring resistances; these dynamic pressures are sent to a proportional member which controls the control valve in the anesthetic gas feed line depending on the value of the difference between the two dynamic pressures so that the anesthetic gas flow cannot exceed a certain value in relation to the oxygen flow. It is thus ensured for the patient that the fresh gas fed in will contain at least a defined ratio of oxygen concentration, e.g., 25 vol. %. The detailed design of such a proportional valve is described in EP-B1-39932.

Before the fresh gas enters the respiration system, it is also passed through an anesthetic vaporizer which enriches the fresh gas with anesthetic vapor. The additional volume percent of anesthetic in the fresh gas leads to a certain reduction of the oxygen concentration compared with the value determined in front of the gas ratio control device. If a low volume percent of anesthetic is metered in, the deviation is slight and is normally on the order of magnitude of the tolerance range of the gas ratio control device. This will be illustrated on the basis of a numerical example. If a halothane stream of 0.4 L is mixed with a fresh gas stream consisting of 2.5 L oxygen and 7.5 L laughing gas, the percentage of oxygen will decrease from 25% without halothane to 24% with halothane. A halothane stream of 0.4 L means in this case a setting of 4 vol. % on the metering adjusting member of the anesthetic vaporizer, which corresponds to the usual maximum concentrations for halothane. If, in contrast, anesthetics are used which require higher concentrations in the fresh gas in order to obtain the desired medical effect, the reduction of the oxygen concentration cannot be ignored any longer. If 2.5 L of another anesthetic is metered in instead of 0.4 L halothane, the oxygen concentration will drop from 25% to 20%. The possible solution that presents itself, namely, changing the basic setting of the gas ratio control device to a correspondingly high minimum oxygen concentration value, is ruled out, because the analgesic effect of the anesthetic gases is not fully utilized in the case of anesthetics to be added in low doses.

SUMMARY AND OBJECTS OF THE INVENTION

It is a primary object of the present invention to improve a gas ratio control device so that the oxygen concentration does not drop below the minimum oxygen concentration value in the case of anesthetics to be metered in low and high doses, while the analgesic effect of the anesthetic gases is fully utilized.

This task is accomplished in that at least one of the measuring resistances can be replaced or bridged over with at least one bypass line that contains a throttle point.

The advantage of the present invention essentially lies in the fact that the ratio of oxygen to anesthetic gas can be increased as needed due to the insertable bypass line with the throttle point, i.e., the oxygen concentration can be increased when an anesthetic to be metered in a high dose is used. The bypass line with the throttle point is either connected in parallel to the corresponding measuring resistance, or it replaces the measuring resistance, as a result of which the dynamic pressure is determined in this case solely by the throttle point of the bypass line.

If the dynamic pressure is to be reduced, the bypass line is generally connected in parallel to the measuring resistance. If the dynamic pressure must be increased, the measuring resistance is replaced with the bypass line. Besides one bypass line, a plurality of bypass lines with a throttle point may also be present, such that they bridge over or replace the measuring resistance one by one or in a combination. Thus, a finer setting of the ratio of oxygen to anesthetic gas for the gas ratio control and better adaptation to the anesthetic concentration set are achieved. It is advantageous to arrange the bypass line at the second measuring resistance.

To insert the bypass, it is useful to provide a reversing valve in the bypass line. If a plurality of bypass lines are present, each bypass line contains such a reversing valve. Depending on the anesthetic used and the concentration setting on the metering adjusting member of the anesthetic vaporizer, the corresponding bypass lines with the throttle points are activated by means of the reversing valves.

It is advantageous to actuate the reversing valve of the bypass line by the metering adjusting member of the anesthetic vaporizer. To do so, the reversing valve may be designed as a pushbutton which is actuated by the metering adjusting member and performs the reversing function at a corresponding angular position of the metering adjusting member.

If the metering adjusting member is provided with a switching surface that extends on the circumference and has a shoulder that can be brushed over by the reversing valve by means of a sensor performing stroke movements, the reversing function begins at the preselected rotation angle at which the shoulder is located. The switching surface may also be designed so that a plurality of reversing valves are switched over at different rotation angles due to a plurality of shoulders being present, so that the corresponding bypass lines can be inserted.

In addition to inserting one or several throttle points as needed, it is advantageous to design the throttle point as a throttle valve whose degree of opening can be changed by the sensor that is in contact with the switching surface of the metering adjusting member. To achieve this, the switching surface is designed at least partially as an oblique plane via which the sensor can be actuated by performing stroke movements.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
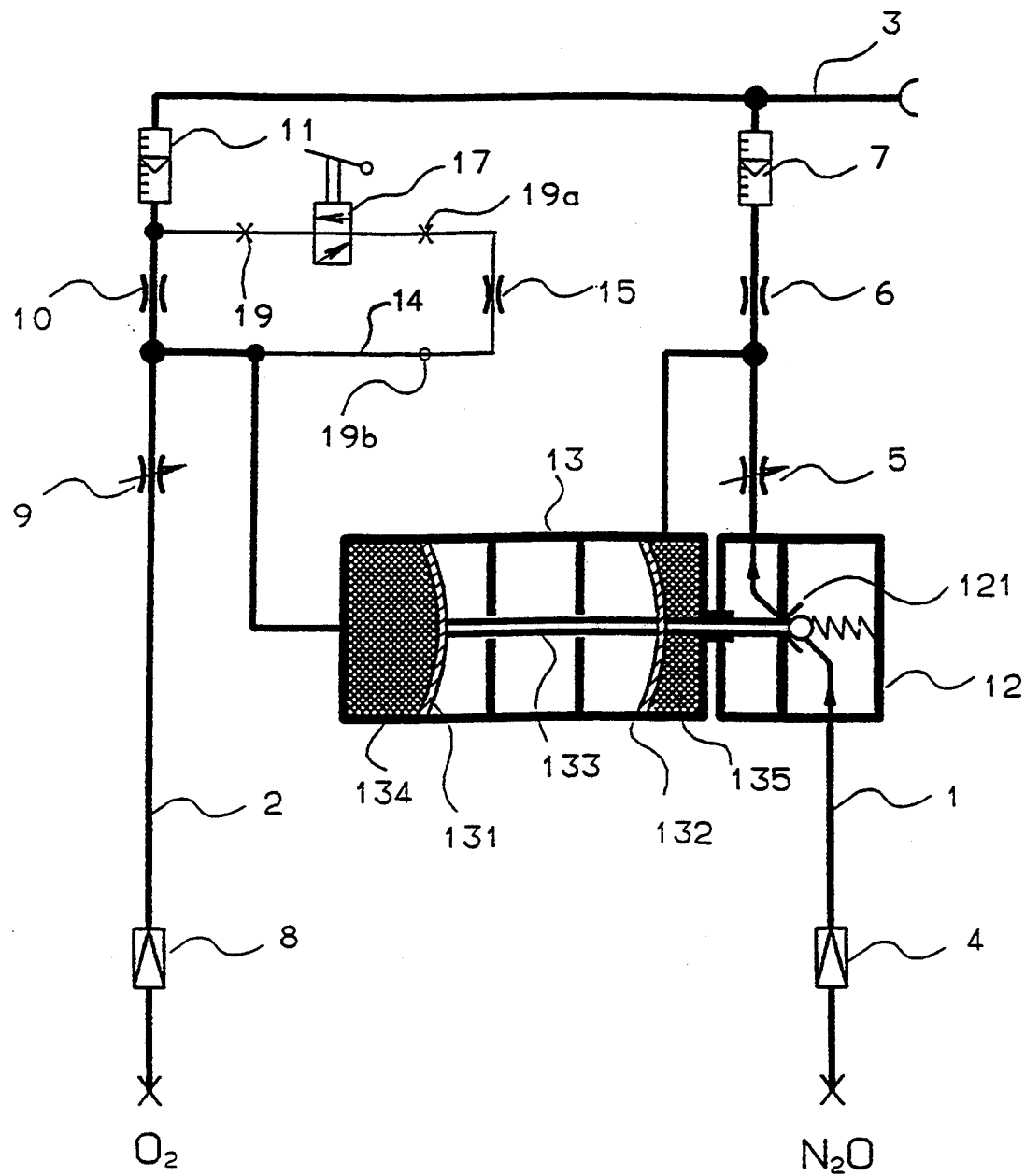
FIG. 1 is a schematic representation of a gas ratio control device with a bypass line.

In the gas ratio control device shown in FIG. 1, an anesthetic gas feed line 1 and an oxygen feed line 2 are united together in a fresh gas outlet 3. The fresh gas outlet 3 is followed by an anesthetic vaporizer, which is not shown in FIG. 1. The anesthetic feed line 1 contains a first pressure reducer 4, an anesthetic gas adjusting valve 5, a first flow resistor or measuring resistance 6, as well as a first flow-measuring tube 7. Analogously, a second pressure reducer 8, an oxygen adjusting valve 9, a second flow resistor or measuring resistance 10, and a second flow-measuring tube 11 are provided in the oxygen feed line 2. A control valve 12, which is controlled via a proportional member 13 responding to the differential pressure occurring in front of the measuring resistances 6 and 10, is located between the first pressure reducer 4 and the anesthetic gas adjusting valve 5 in the anesthetic gas feed line 1. The proportional member 13 consists of a first diaphragm 131 and a second diaphragm 132, which are connected via a bar 133. The diaphragms 131, 132 define a first pressure chamber 134, to which an oxygen control pressure taken from the second measuring resistance 10 is admitted, and a second pressure chamber 135, on which an anesthetic gas control pressure taken from the first measuring resistance 6 acts.

Depending on the value of the oxygen control pressure in relation to the anesthetic gas control pressure, the bar 133 is deflected to the right or left. The control valve 12 consists of a spring-tensioned ball valve 121 which can be opened or closed by the bar 133. The anesthetic gas stream in the anesthetic gas feed line 1 can be reduced or completely shut off with the ball valve 121. The ball valve 121 is located, e.g., in the blocking position when the oxygen control pressure has dropped and the first diaphragm 131 together with the bar 133 is deflected to the left. The feed of anesthetic gas is controlled by the interaction between the oxygen control pressure and the anesthetic gas control pressure, and it is ensured that the minimum oxygen concentration cannot drop below 21%.

The oxygen control pressure and the anesthetic gas control pressure exert the following effects on the oxygen concentration at the fresh gas outlet: If, for example, the anesthetic gas stream is to be reduced by means of the control valve 12 and the oxygen concentration at the fresh gas outlet 3 is consequently to be increased at the identical setting of the oxygen adjusting valve 9 and the anesthetic gas adjusting valve 5, the oxygen control pressure in the first pressure chamber 134 must be reduced, i.e., the dynamic pressure effect at the second measuring resistance 10 must be reduced. To achieve this, the second measuring resistance 10 can be bridged over by the bypass line 14, which contains a throttle point 15 and a reversing valve 17, wherein the reversing valve 17 is shown in FIG. 1 in the open position, i.e., with the bypass switched off.

Figure 2:
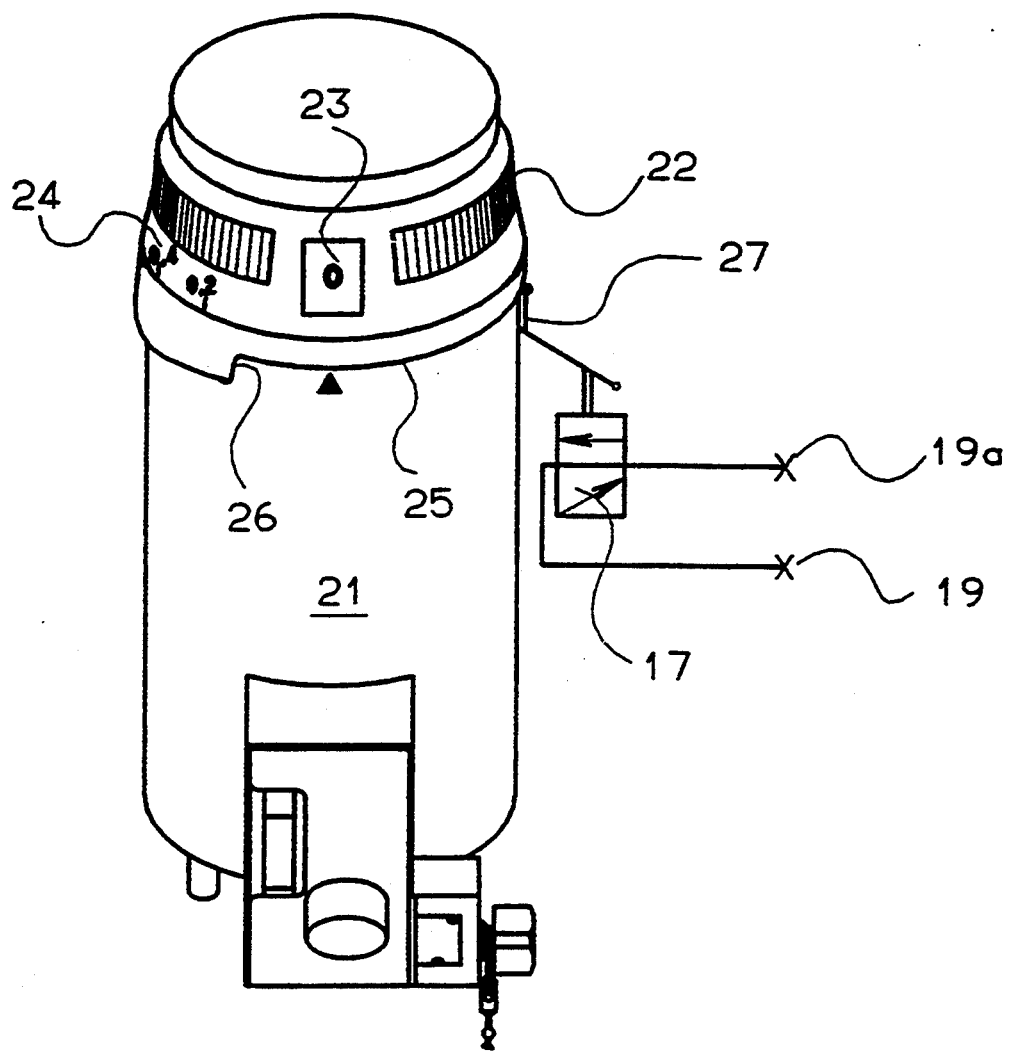
FIG. 2 is a gas ratio control device on an anesthetic vaporizer.

FIG. 2 shows an anesthetic vaporizer 21 with a handwheel 22 as a metering adjusting member which is provided with a zero point key 23 and a scale 24 for setting the anesthetic concentration. The handwheel 22 is provided on the underside with a circular switching surface 25 with a shoulder 26, wherein the switching surface 25 is brushed over by a sensor 27 of the reversing valve 17. The reversing valve 17 is connected to the circuit shown in FIG. 1 by means of the terminals 19, 19a. The anesthetic vaporizer 21 is connected to the fresh gas outlet 3, FIG. 1, and anesthetic gas and oxygen flow through it. The connection of the fresh gas outlet 3 is located on the rear side of the anesthetic vaporizer 21 and is not shown in FIG. 2.

If the handwheel 22 is now actuated by depressing the zero point key 23 and rotated counterclockwise, the sensor 27 will slide along the switching surface 25, depending on the concentration setting. If the sensor 27 brushes over the shoulder 26 (corresponding to a higher concentration setting), the reversing valve 17 switches over to the closed position, and the bypass with the bypass line 14 is connected. Due to the bypass, the differential pressure changes at the proportional control element 13 so that a higher percentage of oxygen in relation to anesthetic gas is set at the control valve 12. The shoulder 26 at the switching surface 25 is associated with a certain concentration value of the scale 24.

Figure 3:
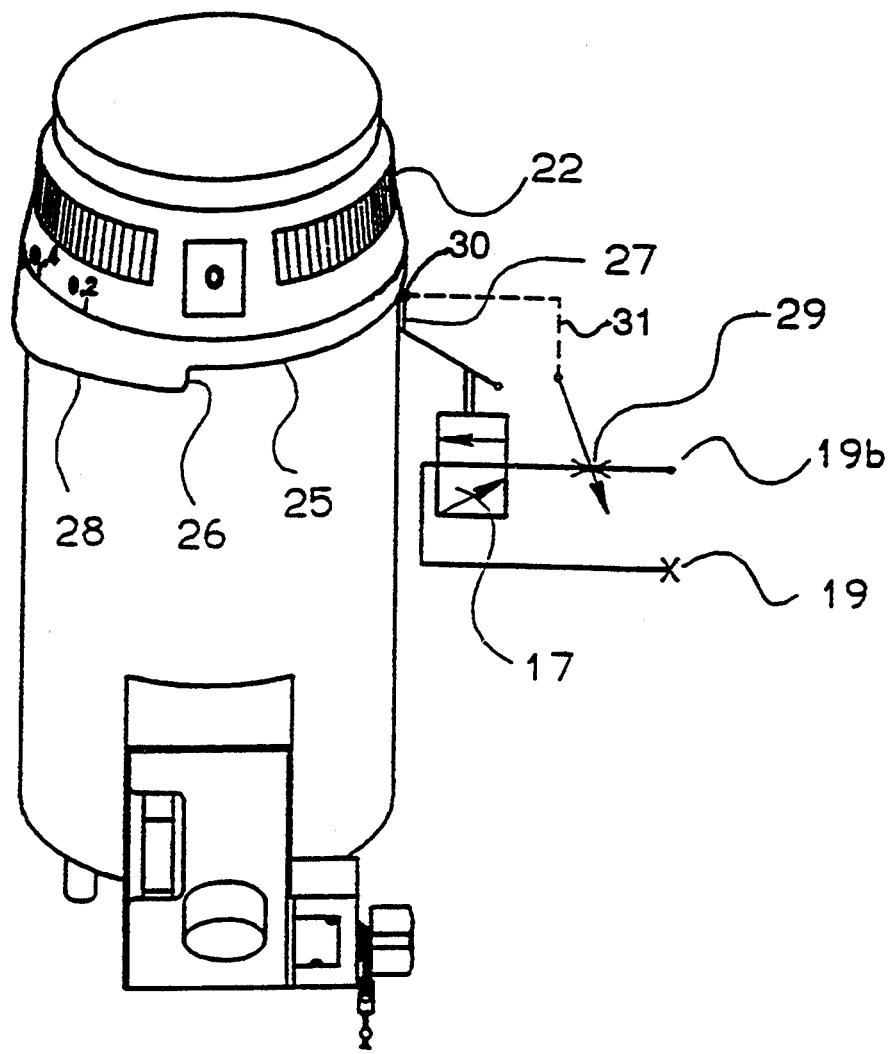
FIG. 3 is a gas ratio control device on an anesthetic vaporizer with a variable throttle valve in the bypass.

FIG. 3 shows an alternative embodiment to FIG. 2 with an adjustable throttle valve 29 instead of the throttle point 15 in FIG. 1. Identical components are designated by the same reference numerals as in FIG. 1 and FIG. 2. The throttle valve 29 is controlled by transmission means 30 which includes the sensor 27 connected to the throttle valve 29 controlling the flow cross section of the throttle valve 29 via connection 31 (shown schematically), depending on the deflection of the sensor 27. The deflection of the sensor 27 is brought about by the switching surface 25 which is designed as an oblique surface 28 behind the shoulder 26. The reversing valve 17 and the throttle valve 29 are connected to the terminals 19, 19b of the circuit shown in FIG. 1.

During rotation of the handwheel 22, the reversing valve 17 is switched over to the closed position when the shoulder 26 is brushed, as a result of which the bypass with the bypass line 14 is switched on. When the sensor 27 subsequently slides on the oblique surface 28, the degree of opening of the throttle valve 29 is changed corresponding to its deflection, and different differential pressures, which are proportional to the concentration set and cause the anesthetic stream to be reduced and the oxygen concentration to be increased, become established on the proportional control element 13.

While specific embodiments of the invention have been shown and described in detail to illustrate the application of the principles of the invention, it will be understood that the invention may be embodied otherwise without departing from such principles.

What is claimed is:

1. A gas ratio control device for anesthetic apparatus, comprising:
   an anesthetic gas line which contains in series connection a control valve, an anesthetic gas adjusting valve and an anesthetic flow resistor;
   an oxygen feed line which contains in series connection an oxygen adjusting valve and an oxygen flow resistor;
   a gas outlet connected to said anesthetic gas line and connected to said oxygen feed line, said gas outlet providing a mixture of oxygen and anesthetic gas;
   a proportional member connected upstream of said anesthetic flow resistor and connected upstream of said oxygen flow resistor and connected to said control valve for controlling said control valve based on a differential pressure formed based on pressure upstream of said anesthetic gas flow resistor and pressure upstream of said oxygen flow resistor;
   bridging means for bridging over at least one of said anesthetic gas flow resistor and said oxygen flow resistor with at least one bypass line containing a throttle point thereby changing said differential pressure and changing a proportion of oxygen to anesthetic gas at said gas outlet.

2. A gas ratio control device according to claim 1, wherein said bypass line contains a reversing valve which terminates bypassing around said at least one measuring resistance.

3. A gas ratio control device according to claim 2, further comprising: an anesthetic vaporizer with a metering adjusting member, said reversing valve being connected to said metering adjusting member for actuation of said reversing valve by said metering adjusting member.

4. A gas ratio control device according to claim 3, wherein said throttle point is designed as a throttle valve, transmission means for changing a resistance of said throttle valve as a function of an opening position of said metering adjusting member, said transmission means being positioned between said throttle valve and said metering adjusting member.

5. A gas ratio control device according to claim 4, wherein said transmission means includes a sensor positioned on an oblique surface connected to said metering adjusting member, said sensor being brought by said oblique surface into a deflected position that is proportional to a setting of said metering adjusting member.

6. A gas ratio control device for an anesthetic apparatus, comprising:
   an anesthetic gas line which contains in series connection a control valve, an anesthetic gas adjusting valve and an anesthetic flow resistor element;
   an oxygen feed line which contains in series connection an oxygen adjusting valve and an oxygen flow resistor element;
   a gas outlet connected to said anesthetic gas line and connected to said oxygen feed line, said gas outlet providing a mixture of oxygen and anesthetic gas;
   proportional means connected to said control valve for controlling said control valve based on a difference between pressure sensed upstream of said anesthetic gas flow resistor element and pressure sensed upstream of said oxygen flow resistor element for opening and closing said control valve to maintain a proportion of oxygen to anesthetic gas based on said measured difference in pressure;
   an anesthetic vaporizer with a metering adjusting member, said anesthetic vaporizer being connected to said gas outlet;
   bridging means for bridging over said oxygen flow resistor element, said bridging means including at least one bypass line containing a throttle point and containing reversing valve means for opening said bypass line, to bypass said oxygen flow resistor element and for closing said bypass line; and,
   a connection between said metering adjusting member and said reversing valve for actuating said reversing valve depending upon a position of said metering adjusting member corresponding to a certain concentration value set at said anesthetic vaporizer.

7. A gas ratio control device according to claim 6, wherein said connection between said metering adjusting member and said reversing valve includes a circular switching surface provided on said metering adjusting member and a sensor positioned for sliding along said switching surface upon changing position of said metering adjusting member.

8. A gas ratio control device according to claim 6, wherein the throttle point includes a throttle valve, said connection including transmission means for changing a resistance of said throttle valve as a function of an opening position of said metering adjusting member.

9. A gas ratio control device for an anesthetic apparatus, comprising:
   an anesthetic gas line which contains in series connection a control valve, an anesthetic gas adjusting valve and an anesthetic flow resistor element;
   an oxygen feed line which contains in series connection an oxygen adjusting valve and an oxygen flow resistor element;
   a gas outlet connected to said anesthetic gas line and connected to said oxygen feed line, said gas outlet providing a mixture of oxygen and anesthetic gas;
   proportional means connected to said control valve for controlling said control valve based on a difference in pressure between a first pressure measuring point upstream of said anesthetic gas flow resistor element and downstream of said anesthetic gas adjusting valve and a second pressure measuring point upstream of said oxygen flow resistor element and downstream of said oxygen adjusting valve, said proportional means for opening and closing said control valve to maintain a proportion of oxygen to anesthetic gas based on said measured difference in pressure; bridging means connecting said second pressure measuring point to said oxygen feed line downstream of said oxygen flow resistor element, said bridging means for bridging over said oxygen flow resistor element, said bridging means including at least one bypass line containing a throttle point and containing a reversing valve for opening said bypass line, to bypass said oxygen flow resistor element, and for closing said bypass line.

10. A gas ratio control device according to claim 9, further comprising:
   an anesthetic vaporizer with a metering adjusting member, said anesthetic vaporizer being connected to said gas outlet; and
   a connection between said metering adjusting member and said reversing valve for actuating said reversing valve depending upon a position of said metering adjusting member.

* * * * *